(12) United States Patent
Pohndorf (10) Patent No.: US 6,228,052 B1
(45) Date of Patent: May 8, 2001

(54) DILATOR FOR INTRODUCER SYSTEM HAVING INJECTION PORT

(75) Inventor: Peter J. Pohndorf, Stillwater, MN (US)

(73) Assignee: Medtronic Inc., Minneapolis, MN (US)

( * ) Notice: Subject to any disclaimer, the term of this patent is extended or adjusted under 35 U.S.C. 154(b) by 482 days.

(21) Appl. No.: 08/608,920

(22) Filed: Feb. 29, 1996

(51) Int. Cl.$^7$ .................................................. A61M 31/00
(52) U.S. Cl. .................................... 604/96.01; 604/93.01; 604/514; 604/104; 604/164.1
(58) Field of Search .................... 604/49, 51–3, 604/93, 96, 103–104, 158, 160–161, 163–164, 170–171, 173, 263–264, 272, 280, 283–284; 128/656–8; 606/191, 194

(56) References Cited

U.S. PATENT DOCUMENTS

| | | |
|---|---|---|
| 3,734,100 | 5/1973 | Walker et al. . |
| 3,890,976 | 6/1975 | Bazell et al. . |
| 4,329,993 | 5/1982 | Lieber et al. . |
| 4,360,031 | 11/1982 | White . |
| 4,411,654 | 10/1983 | Boarini et al. ........................ 604/165 |
| 4,430,081 | 2/1984 | Timmermans ........................ 604/256 |
| 4,850,975 | 7/1989 | Furukawa .............................. 604/170 |
| 4,906,232 * | 3/1990 | Reynolds .............................. 604/171 |
| 5,190,528 * | 3/1993 | Fonger et al. ........................ 604/171 |
| 5,219,335 * | 6/1993 | Willard et al. ........................ 604/164 |
| 5,312,355 * | 5/1994 | Lee ........................................ 604/161 |
| 5,409,469 | 4/1995 | Schaerf ................................. 604/282 |
| 5,476,450 * | 12/1995 | Ruggio ................................. 604/104 |
| 5,527,292 * | 6/1996 | Adams et al. ........................ 604/171 |
| 5,536,255 * | 7/1996 | Moss ..................................... 604/161 |
| 5,571,161 * | 11/1996 | Starksen ............................... 604/161 |

FOREIGN PATENT DOCUMENTS

0450221 * 9/1991 (EP) ..................................... 604/171

* cited by examiner

*Primary Examiner*—Anhtuan T. Nguyen
*Assistant Examiner*—Michael M. Thompson
(74) *Attorney, Agent, or Firm*—Thomas F. Woods; Michael J. Jaro; Harold Pattom (57) ABSTRACT

An introducer system for a lead, catheter, probe or the like, employing a dilator and introducer sheath assembly for dilating a body vessel in preparation for introducing the lead, etc., through the lumen of the introducer sheath that provides for the injection of radiopaque contrast media to observe the cause of an impediment to advancement of the assembly into the vessel lumen. The dilator is formed of an elongated dilator body having a guide wire lumen therein for receiving and being advanced over the guide wire and a hub assembly at the proximal end of the guide wire body. An injection lumen is also formed in the dilator body isolated from the guide wire lumen and in fluid communication with a side port formed in the hub assembly and an injection port formed in the distal end of the dilator body. Preferably, the injection port is formed in a tapered distal end portion of the dilator. In use, the guide wire and the dilator/introducer sheath assembly may be retained in situ in the event that the introduction of the assembly is impeded, and contrast media may be injected under pressure through the side port, injection lumen and out the injection lumen so that the impediment may be visualized.

13 Claims, 8 Drawing Sheets

DILATOR FOR INTRODUCER SYSTEM HAVING INJECTION PORT

FIELD OF THE INVENTION

This invention relates generally to an introducer system for a lead or catheter employing a dilator and introducer sheath assembly for dilating a body vessel in preparation for introducing the lead or catheter through the lumen of the introducer sheath that provides for the injection of radiopaque contrast media to observe the cause of an impediment to advancement of the assembly into the vessel lumen.

BACKGROUND OF THE INVENTION

A multi-step procedure is often used to introduce electrical stimulation leads, catheters, probes or the like into a body vessel, most notably into the vascular system, typically the venous system. Generally this procedure consists of inserting a hollow needle into a blood vessel, such as the subclavian vein. A wire guide is then passed through the needle into the interior portion of the vessel. The needle is then withdrawn and an introducer sheath and dilator assembly is then inserted over the wire guide into the vessel. The assembly is advanced into a suitable position within the vessel, i.e. so that the distal end is well within the vessel but the proximal end is outside the patient. Next, the dilator and wire guide are removed from the introducer sheath lumen. The introducer sheath is left in position and therefore offers direct access from outside the patient into the blood vessel lumen. Then, a lead, catheter or the like can be passed through the introducer sheath lumen into the blood vessel lumen and ultimately be positioned in a desired site, e.g., within the patient's selected heart chamber or an associated blood vessel.

Such a system and method is commonly employed for percutaneously introducing pacing leads for permanent or temporary pacemakers or arrhythmia control devices. In the implantable pacemaker context, an implantable pulse generator is electrically connected to the heart by at least one pacing lead, e.g. an endocardial lead introduced transvenously. More specifically, an endocardial lead provides an electrical pathway between the pacemaker pulse generator, connected to the proximal end of the lead, and endocardial tissue, in contact with one or more electrode at the distal end of the lead. Endocardial tissue refers to a specific layer of tissue in the interior of the heart's chambers. In such a manner, electrical pacing pulses emitted by the pacemaker travel through the endocardial lead conductor and depolarize the endocardial tissue of the heart in contact with the electrode(s). The contraction of the heart is effected by the propagation of the evoked depolarization.

Endocardial pacing leads are often placed in contact with the endocardial tissue by passage through a venous access, such as the subclavian vein or one of its tributaries. In such a manner, transvenous endocardial leads offer as an advantage that they may be placed into contact with the heart without requiring major thoracic surgery. Rather, once the transvenous endocardial leads are introduced into a vein and maneuvered therefrom into contact with the heart, the vein access may be closed and the lead connector end may be tunnelled under the skin to the implant site of the pulse generator and attached thereto.

Such pacemaker leads typically have a relatively bulky connector pin assembly at the proximal end, and the introducer sheath is removed from the lead body at the end of the procedure by being split apart. In such a manner, the introducer sheath does not have to be removed over the relatively bulky connector pin assembly at the proximal end of the lead body.

One purpose of this well known procedure is to expand the lumen of the blood vessel accessed at the puncture site so that it can receive the distal end of the lead. The distal tip of the dilator is tapered to expand the blood vessel lumen as it is advanced through it. After the dilator is withdrawn, the sheath maintains the expansion of the blood vessel lumen and provides an introducer lumen for the distal end and body of the lead.

A problem exists in pacemaker patients who have had multiple leads implanted over time. Scar tissue at the site of lead introduction into a blood vessel during implantation has been found to create difficulties with past lead introduction systems. Specifically the relatively tough scar tissue hinders the introduction of a dilator and introducer sheath assembly. Many times, only through use of larger incisions than are otherwise desirable is such an assembly able to be inserted and advanced.

To provide such access under the best of circumstances, the introducer sheath must be flexible in order to permit the introducer sheath to bend and conform with blood vessel curves and bends. After placement in the vessel lumen, the introducer sheath end is substantially parallel to the blood vessel lumen, and a lead which is introduced therethrough is properly aligned with the vessel lumen. If the sheath did not conform to the vessel shape, a lead introduced through its distal end opening would abut against the vessel wall, possibly injuring the vessel wall and damaging the lead.

When an irregularity or scar tissue impediment to advancement of the assembly is encountered, it is necessary to remove the assembly from the incision into the blood vessel and to explore the reasons for it. One approach is to inject a radiopaque dye or contrast medium into the blood vessel lumen and observe it under fluoroscopy to identify any blockage sites, vessel wall perforations, scar tissue or other impediments to advancement. It may be that none are observable, and the procedure is repeated either with the same or with a different combination of dilator and introducer sheath. The same problem may be repeated. Even if blockage sites, perforations or other impediments are observed, the exact relation of the problem with the distal end portion of the assembly cannot be observed because it is no longer in place.

Since the guide wire lumen of the dilator is available, the physician may attempt to inject the dye or contrast media through it alongside the guide wire. It is difficult or not possible to pressurize the injection of the dye or contrast media and it also escapes back out the proximal end opening of the guide wire lumen of the dilator.

SUMMARY OF THE INVENTION

It is therefore an object of the invention to provide a method of visualizing an impediment to the advancement of an introducer sheath and dilator assembly over a guide wire in a blood vessel without removing the assembly or the guide wire.

It is a further object of the present invention to provide an introducer system having a sheath and dilator formed to allow the injection of pressurized radiopaque contrast media at the distal end portion of the assembly to visualize impediments to the advancement of the assembly into the blood vessel lumen.

These objects are met by the present invention which provides an introducer system for a lead, catheter, probe or the like, employing a dilator and introducer sheath assembly advanced over a guide wire for dilating a body vessel in preparation for introducing the lead, etc., through the lumen of the introducer sheath that incorporates the capability of visualizing an impediment in the blood vessel, to the advancement of an introducer sheath and dilator assembly over the guide wire without removing the assembly or the guide wire from the blood vessel.

In particular, means are provided for injecting a radiopaque contrast media into the blood vessel lumen through a further contrast media injection lumen while the dilator remains in position in the blood vessel. The means preferably comprises an injection lumen formed in the dilator body isolated from the guide wire lumen and in fluid communication with a side port formed in a hub assembly at the proximal end of the dilator body and an injection port formed in the distal end of the dilator body. Preferably, the injection port is formed in a tapered distal end portion of the dilator.

In use, the guide wire and dilator/introducer sheath assembly may be retained in situ in the event that the introduction of the assembly is impeded, and contrast media may be injected under pressure through the side port and injection lumen. The impediment may be visualized with the assembly in place, and the assembly may be manipulated to get around the impediment. This advantageously saves time in the procedure and avoids waste.

BRIEF DESCRIPTION OF THE DRAWINGS

The foregoing and other aspects of the present invention will be best appreciated with reference to the detailed description of the invention in conjunction with the accompanying drawings, wherein.

The figures are not necessarily to scale.

DETAILED DESCRIPTION OF THE PREFERRED EMBODIMENTS

It is to be understood that the present invention is not limited to use only in introducing atrial or ventricular pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, that the present invention may be employed in introducing many of various types of therapeutic or diagnostic catheters or probes and is not limited only to the introduction of electrical leads. For purposes of illustration only, however, the present invention is below described in detail in the context of the introduction of endocardial pacing leads.

Figure 1:
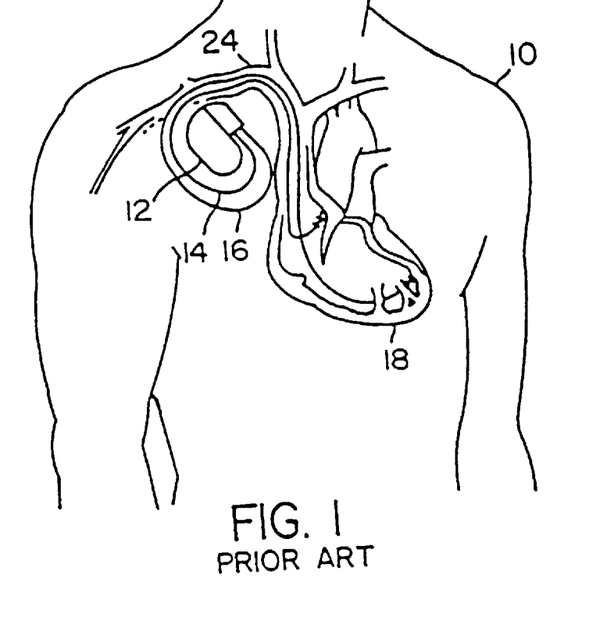
FIG. 1 depicts the venous positioning and placement of transvenous endocardial leads in a patient.

FIG. 1 depicts a typical arrangement of a pacing system implanted in a patient 10, the pacing system comprising a subcutaneously disposed pulse generator 12 and transvenous pacing leads 14 and 16. In FIG. 1, the distal end of pacing lead 14 is shown disposed generally in the atrial region of the patient's heart 18, while the distal end of pacing lead 16 is disposed generally in the ventricular region of heart 18.

Figure 14:
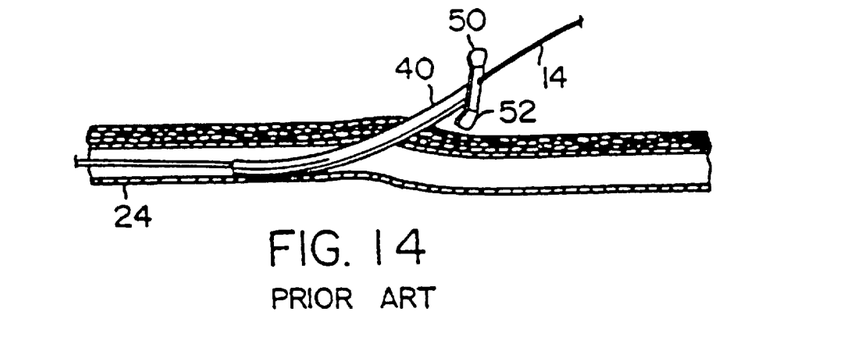
Figure 15:
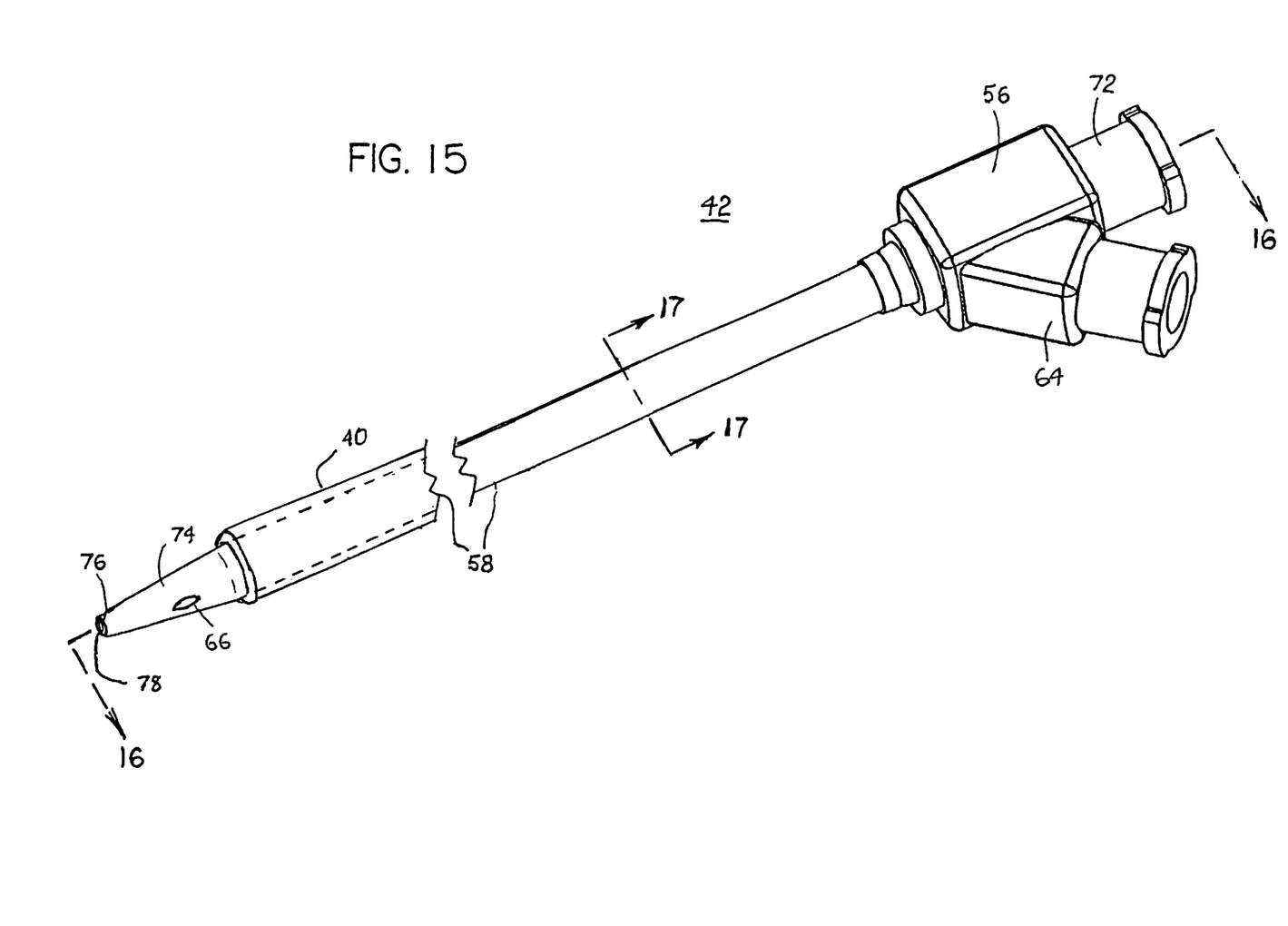
FIG. 15 is a perspective external view of a dilator formed in accordance with the invention for allowing contrast media injection to visualize an impediment to the advancement of an introducer sheath and dilator assembly over a guide wire in a blood vessel without removing the assembly or the guide wire.
Figures 16, 17:
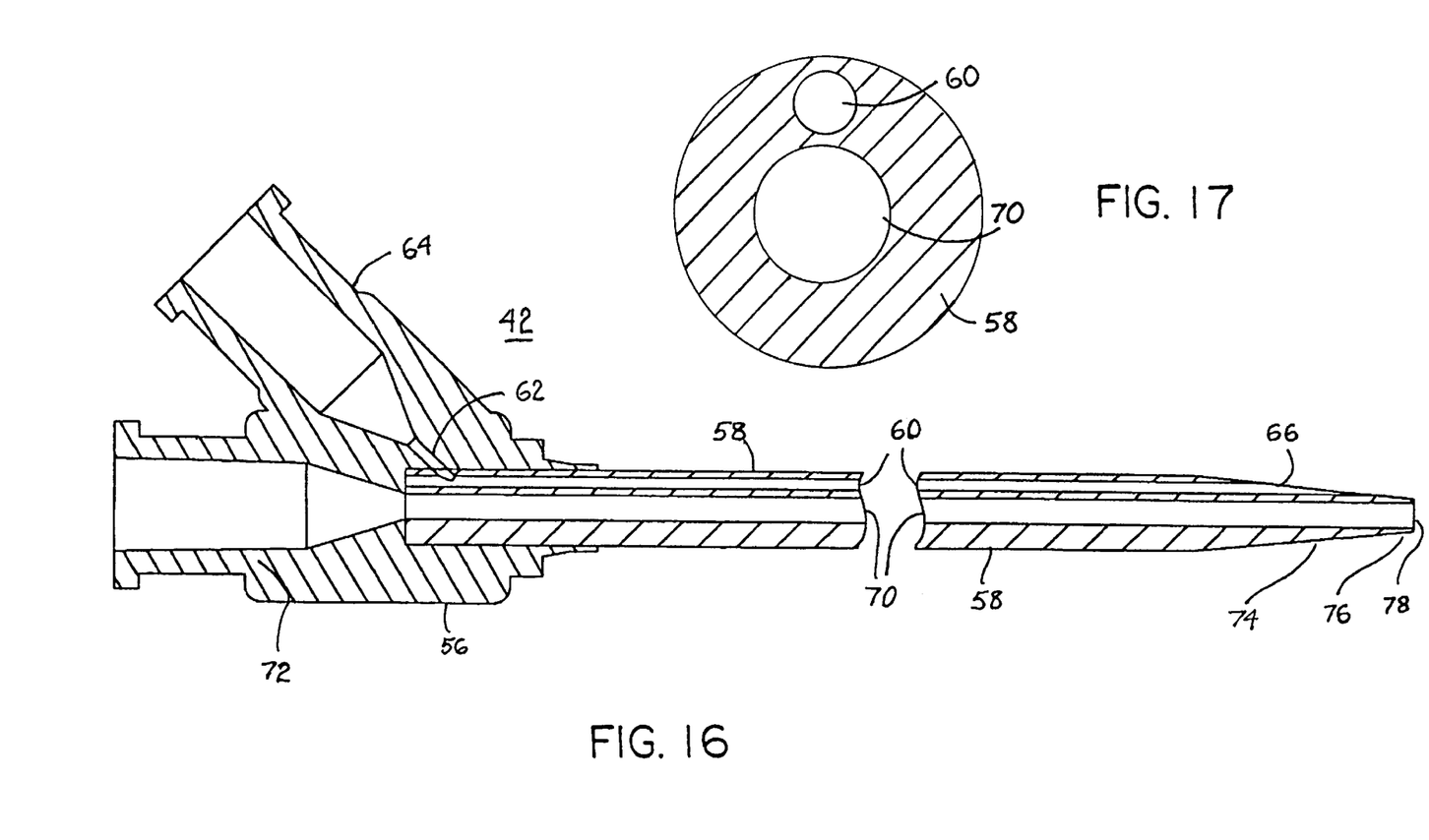
FIG. 16 is a lengthwise cross-section view of the dilator taken along the lines 16—16 of FIG. 15 exposing injection and side port lumens for pressure injection of contrast media.
FIG. 17 is an end cross-section view of the dilator taken along the lines 17—17 of FIG. 15.

The preferred embodiments of the present invention are depicted in FIGS. 15 and 16. The method of lead introduction compatible with an introducer system in accordance with the present invention will be described with reference to the prior art procedure steps illustrated in FIGS. 2 through 14 referenced to the introduction of a pacing lead of FIG. 1 into a body vessel. The introducer system of the present invention may also be used in the introduction of catheters and probes into any similar body vessel, including blood vessels, using the steps illustrated in FIGS. 2 through 14.

Figure 2:
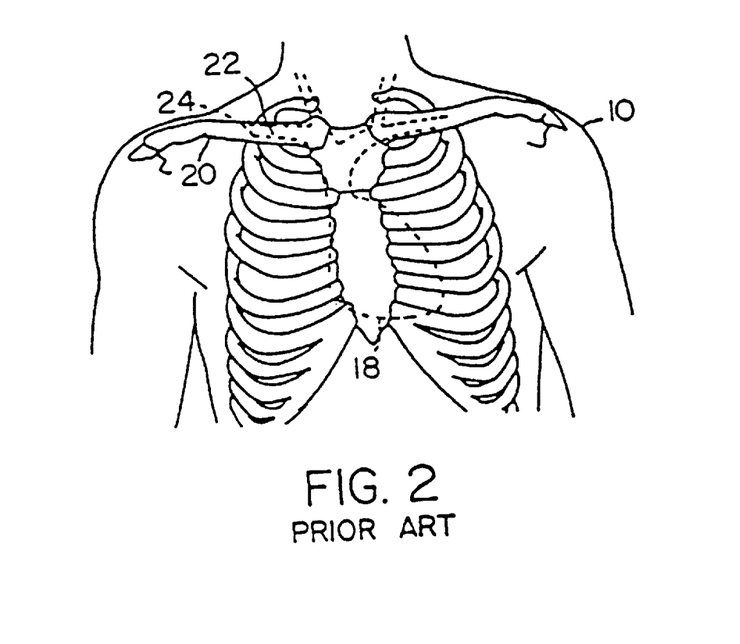
FIG. 2 depicts an appropriate entry site for implantation of a transvenous endocardial lead.

Referring to FIG. 2, and in accordance with common practice in the medical arts, the entry site for a subclavian vein puncture is commonly chosen to be just below and slightly medial to the junction of the middle and inner third of the clavicle 20, at an area designated generally as 22 in FIG. 2. In FIG. 2, the patient's subclavian vein 24 and heart 18 are shown in phantom.

With respect to FIGS. 3–14, it should be understood that they are intended to illustrate the procedure in some detail but are not to scale. Specifically, the blood vessel or vein 24 is enlarged considerably relative to the apparatus that is described below from what is encountered at the subclavian puncture site and is typically encountered at any site in the body. The lumen of vein 24 is typically large enough to accommodate a needle and/or guide wire but must be enlarged to accommodate the sheath for allowing the eventual introduction of the lead, catheter or probe. Fortunately, while vein or other blood of body vessel walls are fragile, they are flexible and can typically be enlarged considerably. This enlargement of the vein lumen is not specifically shown in FIGS. 9–14, but it should be understood that it does take place.

Figure 3:
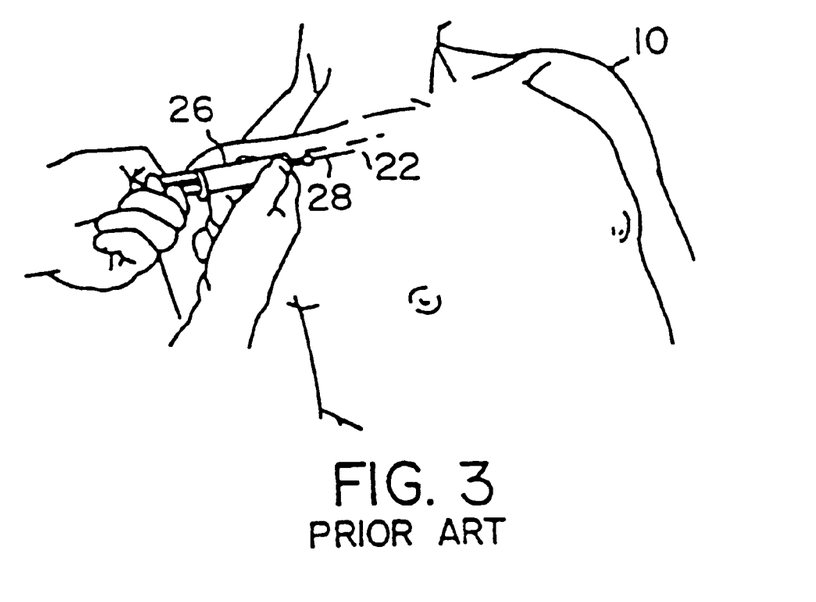
FIGS. 3–14 depict successive stages of introducing a transvenous endocardial lead into a vein.
Figure 4:
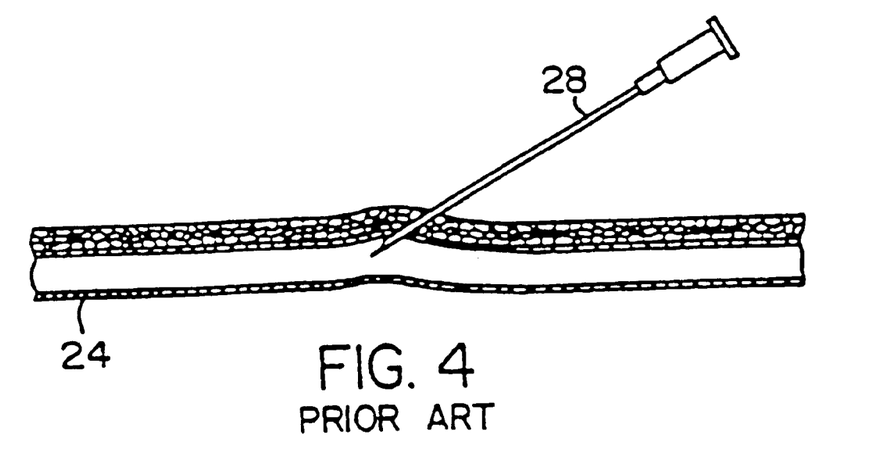

Turning to FIG. 3, the subclavian vein puncture is accomplished by the physician using a disposable syringe 26 having a thin-wall needle 28 detachably connected thereto. Aspiration is performed as the needle is advanced into the subclavian vein, to verify proper needle placement within vein 24. Next, aspirating syringe 26 is disconnected from needle 28, which remains in vein 24 as shown in FIG. 4. Typically, the physician will place his or her finger over the needle to avoid air aspiration and excessive bleeding.

Figure 5:
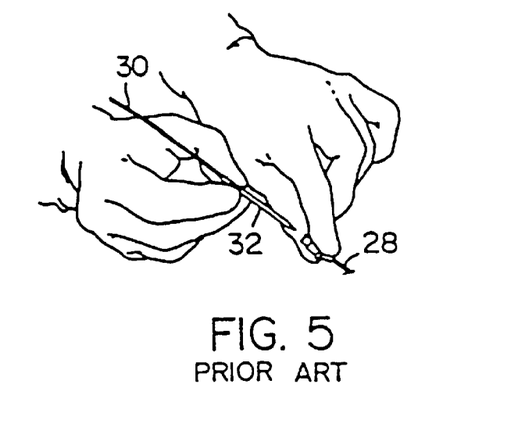
Figure 6:
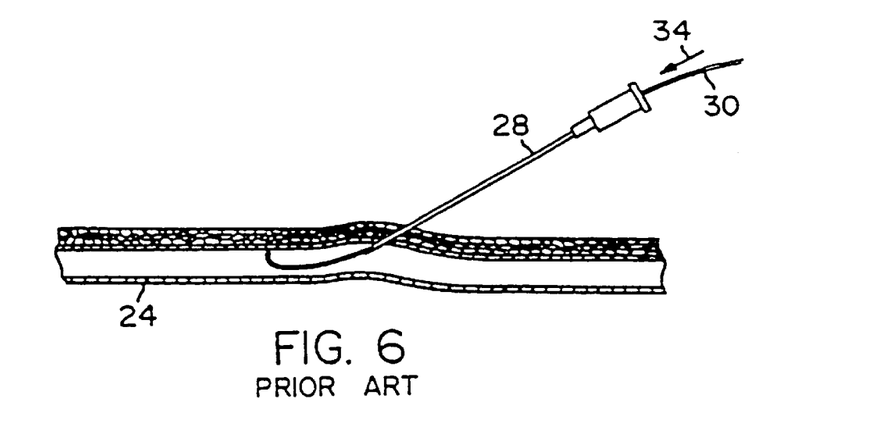
Figure 7:
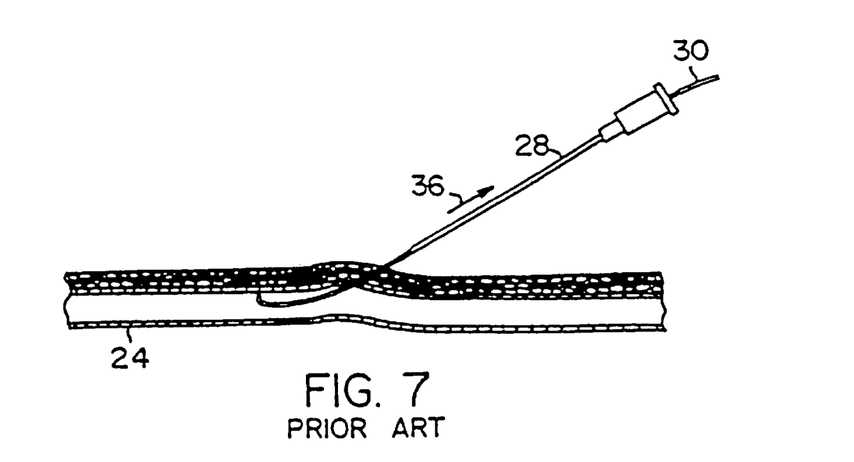

The next step in the lead implantation procedure involves insertion of a conventional J-type guide wire 30 through needle 28, as illustrated in FIG. 5. Typically, guide wire 30 is equipped with a tip deflector 32 for facilitating insertion of wire 30 into the lumen of needle 28. As shown in FIG. 6, as wire 30 is fed through needle 28 in the direction of arrow 34, the distal end of wire 30 exits the tip of needle 28, and wire 30 regains its "J" shape within vein 24. Once guide wire 30 has entered vein 24, needle 28 is withdrawn in the direction of arrow 36 in FIG. 7, leaving wire 30 in place. Guide wire 30 is advanced along vessel 24 until its distal end is disposed generally in the area of the patient's superior vena cava, leaving approximately 15–20 cm of the proximal end of guide wire 30 exposed.

Figure 8:
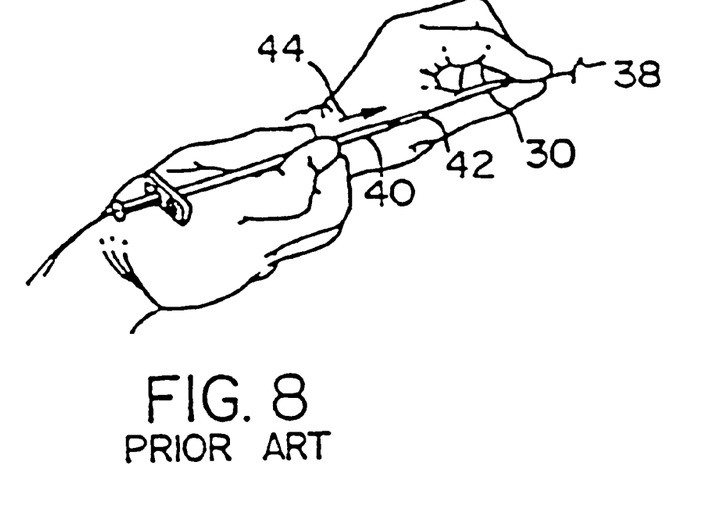
Figure 9:
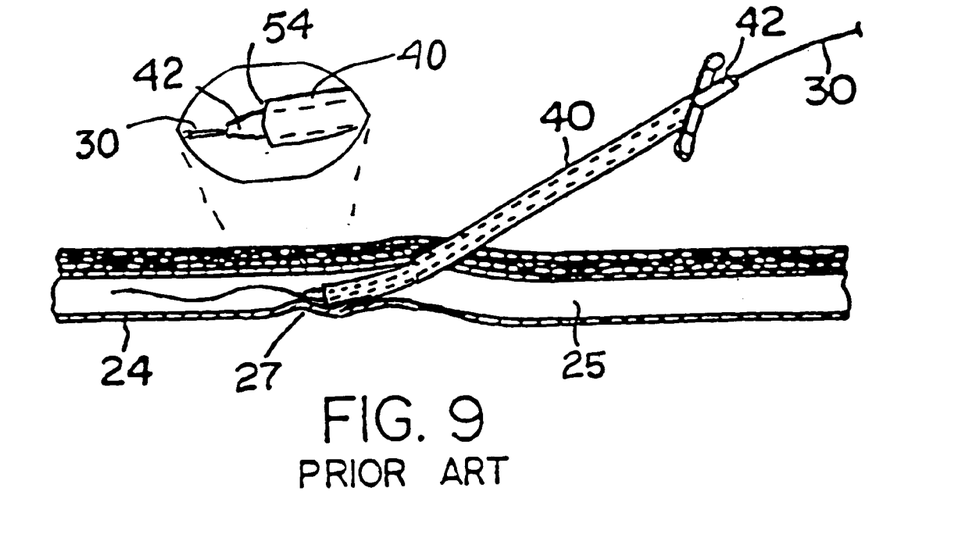

A small skin incision 38 is made at the guide wire entry site, parallel to clavicle 20, as shown in FIG. 8. In the next stage of the implantation procedure, an introducer sheath 40 with vessel dilator 42, as an assembly, are threaded onto the proximal end of wire 30. Dilator 42 has a tapered distal end portion for dilating the lumen of body vessel or vein 24 on advancement of the distal end portion into the vein lumen. The dilator 42 has a cylindrical tubular body with a generally constant major diameter proximal to the tapered distal end portion enclosing a dilator lumen having proximal and distal end openings for receiving the guide wire so that the assembly can be advanced it. The sheath 40 also has an elongated tubular body of relatively constant outside diameter and an inner sheath lumen allowing it to be fitted over the dilator 42 proximal to the tapered distal end portion. Sheath 40 and dilator 42 are advanced in the direction of arrow 44, through the subclavian fascia and into subclavian vein 24, until a short length (e.g., 2–8 cm) of sheath 40 and vessel dilator 42 remain exposed, as shown in FIG. 9.

In the prior art, the junction of the sheath 40 distal end over the dilator 42 outer surface presents a bull nose or annular step 54 which, however slight it may appear to be to the eye, can catch on the blood vessel wall during this advancement. As mentioned above, the distal end portion of the sheath 40 may also be tapered to diminish the height of the step 54, but some step height has to remain in order to preserve the integrity of the sheath 40 (i.e., to prevent it from tearing or rolling up) and to provide enough column strength to allow it to be manipulated in the vein lumen when the dilator 42 is removed.

Curves, bends or other irregularities or other impediments 27 of the vein 24 can cause the step 54 to catch and impede progress, injure the wall of the vein 24 and/or mis-align the introducer sheath lumen with the lumen 25 of vein 24. As also mentioned above, the wall of vein 24 may have scar tissue from prior procedures forming impediment 27 and make the introduction past it even more difficult.

Figure 10:
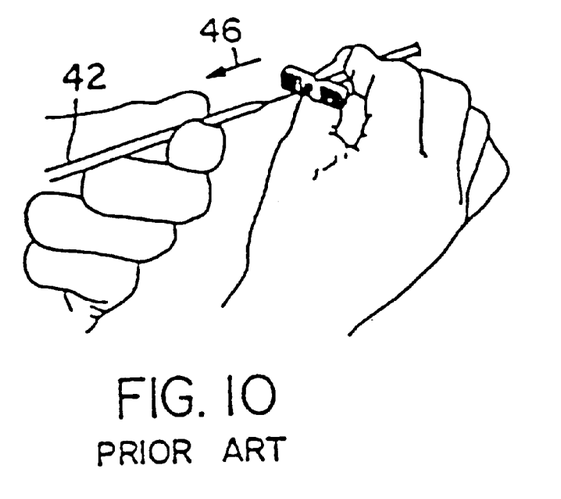
Figure 11:
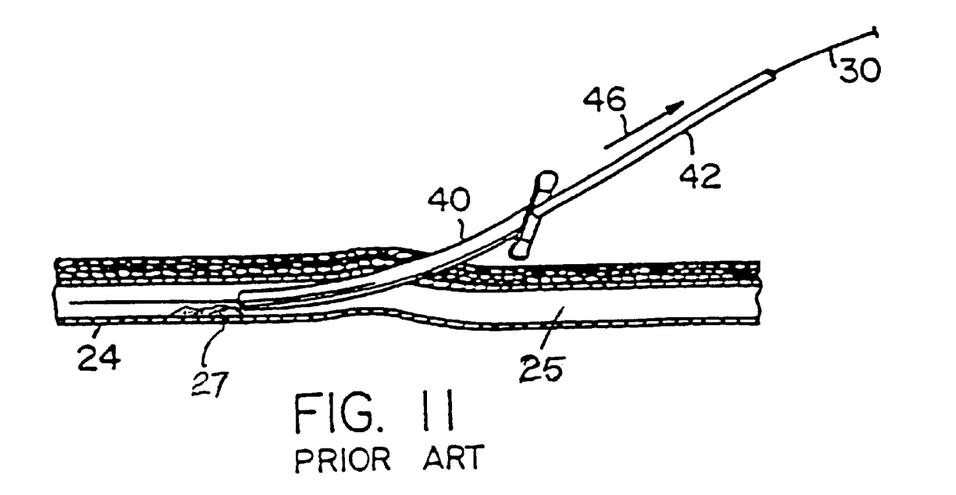

Next, as shown in FIGS. 10 and 11 (and assuming no such complications for purposes of completing the description of the procedure), vessel dilator 42 is withdrawn in the direction of arrow 46, and sheath 40 is introduced further within subclavian vein 24, leaving introducer sheath 40 and guide wire 30 in place with its distal end disposed within subclavian vein 24. Guide wire 30 may be removed at this point as well, although it may be left in place in case the lead needs to be repositioned or reinserted. As shown in FIG. 11, introducer sheath 40 must bend to conform to the shape of subclavian vein 24 to provide an unobstructed conduit for the pacing lead to be introduced. Through such curvature, moreover, the lead may be introduced so as to be aligned axially with vein 24 and not abut and damage wall 25 of subclavian vein 24.

Figures 12, 13:
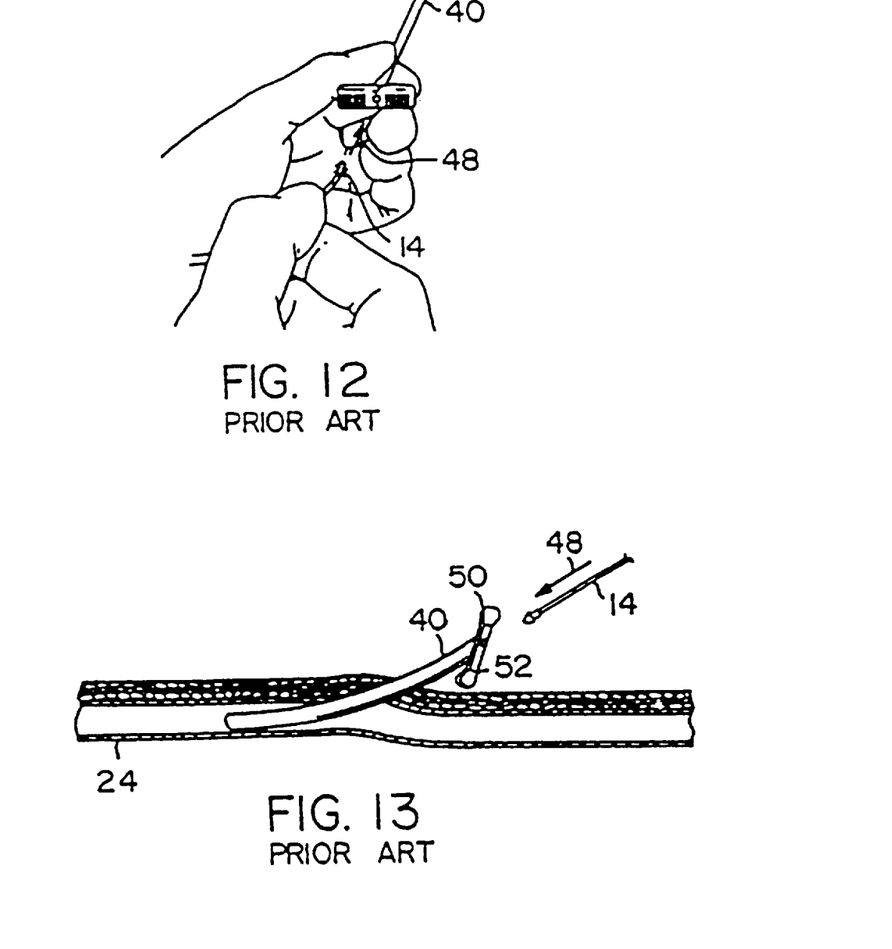

In the final stages of the lead implantation procedure, illustrated in FIGS. 12–14, pacing lead 14 is inserted into the proximal end of introducer sheath 40 in the direction of arrow 48, and advanced into the desired position within patient 10 through vein 24. Lastly, introducer sheath 40 is removed. Removal of introducer sheath 40 may be accomplished in one of several known ways, depending upon the particular type of introducer sheath 40. Preferably, sheath 40 includes means for permitting removal of sheath 40 from a lead disposed therethrough without requiring sheath 40 to be removed from an end of the lead.

In particular, introducer sheath 40 is split apart by grasping tabs 50 and 52 as it is being withdrawn from the lead introduction site. In the preferred embodiment linear scoring lines or other weakened line structures extend along the length of and within the wall of sheath 40 as shown in Boarini et al. U.S. Pat. No. 4,411,654 and Vegoe et al U.S. Pat. No. 5,180,372, both incorporated herein by reference. Such weakened line structures may consist of material having the physical property of molecular orientation, whereby a tear in the material runs readily only in a longitudinal direction along the length of sheath 40. Whichever linear structure or modification of the sheath wall is employed, sheath 40 may be longitudinally split into two by grasping and pulling tabs 50 and 52 apart. Other sheaths are known which are severable by means of a special slitter device or the like.

As shown in FIG. 1, pacemaker pulse generator 12 may be coupled with two pacing leads 14 and 16 introduced percutaneously and transvenously in the manner described above. In that case, as with single-lead implants, it may be necessary to keep guide wire 30 in place until after the first lead has been implanted. Thus, as previously noted with reference to FIGS. 10 and 11, guide wire 30 may be left in place when dilator 42 is withdrawn. The first lead, if it is sufficiently small, may be introduced into subclavian vein 24 alongside guide wire 30. The first introducer sheath is then removed leaving guide wire 30 in place. A second assembled introducer sheath and vessel dilator can then be guided along guide wire 30 in the same manner as the first assembled sheath/dilator, before guide wire 30 is finally removed.

As mentioned above, the above described procedure may also be used in the introduction and placement of catheters or probes in blood vessels or other body vessels.

Turning now to the preferred embodiments of the invention, the dilator 42 is modified from that shown in FIGS. 3–14 to allow contrast media injection to visualize an impediment to the advancement of an introducer sheath and dilator assembly over a guide wire in a blood vessel without removing the assembly or the guide wire. FIG. 15 is a perspective external view of a preferred embodiment of a dilator 42 formed in accordance with the invention. A distal segment of the introducer sheath 40 is also shown in FIG. 15. Introducer sheath 40 is formed of an elongated tubular body having a sheath lumen formed extending between proximal and distal end openings in the proximal and distal ends thereof for receiving the outer surface of the elongated tubular body of the dilator 40 as shown in FIG. 9 and described above.

FIGS. 16 and 17 are cross-section views of the dilator 42 and the elongated tubular dilator body 58 exposing the injection lumen 60 and a side port lumen 62 of side port extension 64 for pressure injection of contrast media out the injection port 66 and into the blood vessel lumen when the assembly is in the position of FIG. 9. A hub assembly 56 is attached at the proximal end of elongated tubular dilator body 58 that is integrally formed with the side port extension 64 and a guide wire port extension 72. The port extensions 64 and 72 include conventional luer lock hubs.

Preferably, the injection port 66 is formed in a tapered distal end portion 74 of the dilator 42. The tapered distal end portion 74 terminates in the dilator distal end 76 and the distal guide wire lumen opening 78 of guide wire lumen 70.

In use, a hypodermic type plunger (not shown) filled with contrast media may be attached to the side port extension 64 before the dilator and introducer sheath assembly is advanced in the manner of the steps of FIGS. 8 and 9. Referring to FIGS. 8 and 9, the injection lumens 58 and 62 may be filled with contrast media before the advancement of the assembly over the guide wire 30 in FIG. 9. Then, if an advancement problem arises with an impediment 27, the plunger may be depressed to inject the contrast media from injection port 66 into the blood vessel lumen 25, and the impediment 27 may be viewed and the assembly manipulated to avoid or overcome it.

Alternatively, the dilator 42 of the present invention may be substituted for a conventional dilator that encounters impediments, and the steps of FIGS. 8 and 9 may be repeated with the contrast media injection as described above.

Through the above described features of the preferred embodiment of the invention, contrast media may be quickly injected while the assembly is in situ and the impediment overcome or fully understood as quickly as possible.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. An introducer system for use with a catheter or lead comprising:

a sheath having a first end and a second end, the sheath being compatible for insertion within a body, the first end configured to insert the sheath within the body with the second end extending out of the body, the sheath having a central lumen configured to permit introduction of at least one lead or catheter therethrough;

means for permitting removal of the sheath from a lead or catheter disposed therethrough without requiring the sheath to be removed from an end of the lead or catheter disposed therethrough; and a dilator having a first distal end and a second proximal end, the first distal end of the dilator being tapered, the dilator configured to be disposed through the central lumen of the sheath;

means integrally formed with the dilator for introducing contrast media adjacent the first distal end thereof with the sheath in place over the dilator body for visualizing an impediment in the blood vessel to the advancement of the sheath and dilator over a guide wire without removing the dilator or the guide wire from the body.

2. The introducer system of claim 1 wherein the visualizing means further comprises:

a contrast injection lumen formed in the dilator body extending between the proximal end thereof and the distal end thereof, the contrast injection lumen terminating in an injection port in the distal end thereof; and injection means in fluid communication with the contrast injection lumen for injecting a radiopaque contrast media into the blood vessel lumen through the further contrast media injection lumen while the dilator remains in position in the blood vessel.

3. An introducer system for dilating a body vessel to percutaneously position an introducer sheath into the body vessel lumen over a guide wire in the blood vessel lumen and for visualizing an impediment in the body vessel lumen impeding advancement of the distal end thereof comprising:

a dilator having an elongated tubular dilator body extending between a proximal end and a distal end and having a guide wire lumen formed therein extending between guide wire lumen openings in said proximal and distal ends for receiving a guide wire therein for dilating the body vessel lumen diameter on advancement of said dilator distal end over the guide wire in the body vessel lumen;

an elongated introducer sheath having a tubular body enclosing a sheath lumen therein and extending between openings in a sheath distal end and a sheath proximal end, said sheath lumen having a lumen diameter for receiving said tubular dilator body inserted therein and forming an introducer sheath and dilator assembly with a dilator distal end portion extending distally of the sheath distal end, the sheath having means for permitting removal of the sheath from a lead or catheter disposed therethrough without requiring the sheath to be removed from an end of the lead or catheter disposed therethrough; and means integrally formed with said dilator for introducing contrast media adjacent the distal end portion extending distally of the sheath distal end thereof with the sheath in place over said tubular dilator body for visualizing an impediment in the blood vessel to the advancement of the introducer sheath and dilator assembly over the guide wire without removing the assembly or the guide wire from the blood vessel.

4. The introducer system of claim 3 wherein:

said elongated tubular dilator body has a tapered distal end portion extending proximally of said distal end, and a dilator outer surface major diameter extending between said dilator body proximal end and said tapered distal end portion, said tapered distal end portion formed with a progressively increasing taper diameter from said distal end to said dilator outer surface major diameter for dilating the body vessel lumen diameter on advancement of said dilator distal end portion through the body vessel lumen.

5. The introducer system of claim 2 wherein said means for visualizing further comprises:

a contrast injection lumen formed in said dilator body extending between said proximal end thereof and said tapered distal end portion, said contrast injection lumen terminating in an injection port in said tapered distal end portion; and injection means in fluid communication with said contrast injection lumen for injecting a radiopaque contrast media into the blood vessel lumen through the further contrast media injection lumen while the dilator remains in position in the blood vessel.

6. The introducer system of claim 3 wherein:

said dilator is formed with a hub assembly coupled to said proximal end of said dilator body having a guide wire lumen port and a side port for attachment to a source of contrast media; and said injection means further comprises a side port lumen in said side port of said hub assembly in fluid communication with the proximal end of said contrast injection lumen.

7. The introducer system of claim 1 wherein said means for visualizing further comprises:

a contrast injection lumen formed in said dilator body extending between said proximal end thereof and said distal end thereof, said contrast injection lumen terminating in an injection port in said distal end thereof; and injection means in fluid communication with said contrast injection lumen for injecting a radiopaque contrast media into the blood vessel lumen through the further contrast media injection lumen while the dilator remains in position in the blood vessel.

8. The introducer system of claim 7 wherein:

said dilator is formed with a hub assembly coupled to said proximal end of said dilator body having a guide wire lumen port and a side port for attachment to a source of contrast media; and said injection means further comprises a side port lumen in said side port of said hub assembly in fluid communication with the proximal end of said contrast injection lumen.

9. An introducer system for dilating a body vessel to percutaneously position an introducer sheath into the body vessel lumen over a guide wire in the blood vessel lumen and for visualizing an impediment in the body vessel lumen impeding advancement of the distal end thereof comprising:

a dilator having an elongated tubular dilator body extending between a proximal end and a distal end and having a guide wire lumen formed therein extending between guide wire lumen openings in said proximal and distal ends for receiving a guide wire therein for dilating the body vessel lumen diameter on advancement of said dilator distal end over the guide wire in the body vessel lumen;

an elongated introducer sheath having a tubular body enclosing a sheath lumen therein and extending between openings in a sheath distal end and a sheath proximal end, said sheath lumen having a lumen diameter for receiving said tubular dilator body inserted therein and forming an introducer sheath and dilator assembly with [a] the dilator distal end portion extending distally of the sheath distal end the sheath having means for permitting removal of the sheath from a lead or catheter disposed therethrough without requiring the sheath to be removed from an end of the lead or catheter disposed therethrouqh; and a contrast injection lumen formed in said dilator body isolated from said guide wire lumen extending between said proximal end thereof and said distal end portion, said contrast injection lumen terminating in an injection port in said distal end, for introducing contrast media adjacent the distal end portion thereof with the sheath in place over said tubular dilator body for visualizing an impediment in the blood vessel to the advancement of the introducer sheath and dilator assembly over the guide wire without removing the assembly or the guide wire from the blood vessel.

10. The introducer system of claim 9 wherein:

said elongated tubular dilator body has a tapered distal end portion extending proximally of said distal end, and a dilator outer surface major diameter extending between said dilator body proximal end and said tapered distal end portion, said tapered distal end portion formed with a progressively increasing taper diameter from said distal end to said dilator outer surface major diameter for dilating the body vessel lumen diameter on advancement of said dilator distal end portion through the body vessel lumen.

11. The introducer system of claim 10 wherein said contrast injection lumen formed in said dilator body terminates in said injection port in said tapered distal end portion.

12. The introducer system of claim 11 wherein:

said dilator is formed with a hub assembly coupled to said proximal end of said dilator body having a guide wire lumen port and a side port having a side port lumen in fluid communication with the proximal end of said contrast injection lumen.

13. A method of introducing an introducer sheath into a body and visualizing an impediment in the body vessel impeding the advancement of the sheath comprising the steps of:

introducing a guide wire distal end into a body with a guide wire proximal end outside an opening to the body;

providing an introducer sheath having means for permitting removal of the sheath from a lead or catheter disposed therethrough without requiring the sheath to be removed from an end of the lead or catheter disposed therethrough, the introducer sheath having an introducer sheath lumen therethrough;

providing a dilator having a guide wire lumen formed therein extending between proximal and distal guide wire lumen openings in the proximal end and distal ends and a contrast media injection lumen formed in the dilator body separate from the guide wire lumen and extending between the proximal end and terminating in an injection port in the distal end;

assembling the dilator into the introducer sheath lumen to form an introducer sheath and dilator assembly;

advancing the distal guide wire lumen opening of the introducer sheath and dilator assembly distally over the guide wire proximal end and into the body vessel; and upon encountering an impediment in the body vessel to advancement of the introducer sheath and guide wire assembly, injecting contrast media through the contrast media injection lumen and distally to the injection port for enabling visualizing of the impediment.

* * * * *

UNITED STATES PATENT AND TRADEMARK OFFICE
CERTIFICATE OF CORRECTION

PATENT NO. : 6,228,052 B1
DATED : May 8, 2001
INVENTOR(S) : Pohndorf

It is certified that error appears in the above-identified patent and that said Letters Patent is hereby corrected as shown below:

Column 9,
Line 30, change "with [a] the" to -- with the --.

Signed and Sealed this

Eighteenth Day of March, 2003

JAMES E. ROGAN
*Director of the United States Patent and Trademark Office*